(12) United States Patent
Boesen et al.

(10) Patent No.: US 12,245,873 B2
(45) Date of Patent: *Mar. 11, 2025

(54) DISPOSABLE SENSOR ARRAY WEARABLE DEVICE SLEEVE SYSTEM AND METHOD

(71) Applicant: BRAGI GmbH, Munich (DE)

(72) Inventors: Peter Vincent Boesen, Munich (DE); Jake Berry Turner, Munich (DE)

(73) Assignee: BRAGI GMBH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,544

(22) Filed: Oct. 25, 2022

(65) Prior Publication Data

US 2023/0067067 A1 Mar. 2, 2023

Related U.S. Application Data (63) Continuation of application No. 15/692,681, filed on Aug. 31, 2017, now Pat. No. 11,490,858.

(Continued)

(51) Int. Cl.
| | | |
|---|---|---|
| *A61B 5/00* | (2006.01) | |
| *A61B 5/11* | (2006.01) | |
| *A61B 5/0205* | (2006.01) | |

(52) U.S. Cl.
CPC .......... *A61B 5/6817* (2013.01); *A61B 5/0002* (2013.01); *A61B 5/1114* (2013.01);
(Continued)

(58) Field of Classification Search
None
See application file for complete search history.

(56) References Cited

U.S. PATENT DOCUMENTS

| | | |
|---|---|---|
| 2,325,590 A | 8/1943 | Carlisle et al. |
| 2,430,229 A | 11/1947 | Kelsey |
| | (Continued) | |

FOREIGN PATENT DOCUMENTS

| | | |
|---|---|---|
| CN | 204244472 U | 4/2015 |
| CN | 104683519 A | 6/2015 |
| | (Continued) | |

OTHER PUBLICATIONS

Akkermans, "Acoustic Ear Recognition for Person Identification", Automatic Identification Advanced Technologies, 2005 pp. 219-223.

(Continued)

*Primary Examiner* — Sana Sahand
(74) *Attorney, Agent, or Firm* — Goodhue, Coleman & Owens, P.C.

(57) ABSTRACT

A removable wearable device sleeve includes a sleeve body, one or more sensors, and an interface for operative communication with the wearable device. A removable sleeve includes a sleeve body having a front element having a first aperture, a back element having a second aperture, a tubular element having a first end and a second end with a third aperture, and one or more back elements define a cavity to encase an earpiece, an interface, and a sensor, wherein the sensor communicates sensor readings to the wearable device through the interface. A method of placing a sensor configured to communicate with a wearable device onto the wearable device includes providing a removable sleeve and inserting the wearable device through the first aperture of the front element into the cavity of the removable sleeve to provide a removable wearable device sleeve.

21 Claims, 9 Drawing Sheets

Related U.S. Application Data (60) Provisional application No. 62/382,043, filed on Aug. 31, 2016.

(52) U.S. Cl.
CPC .......... *A61B 5/002* (2013.01); *A61B 5/02055* (2013.01); *A61B 2560/0214* (2013.01); *A61B 2560/0425* (2013.01); *A61B 2560/045* (2013.01)

(56) References Cited

U.S. PATENT DOCUMENTS

| | | |
|---|---|---|
| 3,047,089 A | 7/1962 | Zwislocki |
| D208,784 S | 10/1967 | Sanzone |
| 3,586,794 A | 6/1971 | Michaelis |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,673,692 A | 10/1997 | Schulze et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin et al. |
| 8,436,780 B2 | 5/2013 | Schantz et al. |
| D687,021 S | 7/2013 | Yuen |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,107,014 B2 | 8/2015 | Tang |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| 9,591,395 B2 | 3/2017 | Burgett et al. |
| D788,079 S | 5/2017 | Son et al. |
| 11,490,858 B2 * | 11/2022 | Boesen ................ A61B 5/1114 |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0035340 A1 | 3/2002 | Fraden et al. |

(56) References Cited

U.S. PATENT DOCUMENTS

| | | |
|---|---|---|
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2003/0220584 A1 | 11/2003 | Honeyager et al. |
| 2004/0070564 A1 | 4/2004 | Dawson et al. |
| 2004/0081328 A1 | 4/2004 | Leedom et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0209516 A1 | 9/2005 | Fraden |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0135717 A1 | 6/2007 | Uenishi et al. |
| 2008/0076972 A1 | 3/2008 | Dorogusker et al. |
| 2008/0090622 A1 | 4/2008 | Kim et al. |
| 2008/0146890 A1 | 6/2008 | LeBoeuf et al. |
| 2008/0254780 A1 | 10/2008 | Kuhl et al. |
| 2008/0255430 A1 | 10/2008 | Alexandersson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0052709 A1* | 2/2009 | Smith .................... H04R 25/02 381/328 |
| 2009/0073070 A1 | 3/2009 | Rofougaran |
| 2009/0097689 A1 | 4/2009 | Prest et al. |
| 2009/0105548 A1 | 4/2009 | Bart |
| 2009/0191920 A1 | 7/2009 | Regen et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2010/0033313 A1 | 2/2010 | Keady et al. |
| 2010/0203831 A1 | 8/2010 | Muth |
| 2010/0210212 A1 | 8/2010 | Sato |
| 2010/0217098 A1 | 8/2010 | LeBoeuf et al. |
| 2010/0320961 A1 | 12/2010 | Castillo et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2012/0057740 A1 | 3/2012 | Rosal |
| 2012/0197093 A1 | 8/2012 | LeBoeuf et al. |
| 2012/0283577 A1* | 11/2012 | LeBoeuf ............ A61B 5/02116 600/479 |
| 2013/0131519 A1 | 5/2013 | LeBoeuf et al. |
| 2013/0316642 A1 | 11/2013 | Newham |
| 2013/0336495 A1 | 12/2013 | Burgett et al. |
| 2013/0346168 A1 | 12/2013 | Zhou et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0110587 A1 | 4/2015 | Hori |
| 2015/0148989 A1 | 5/2015 | Cooper et al. |
| 2015/0245127 A1 | 8/2015 | Shaffer |
| 2016/0033280 A1 | 2/2016 | Moore et al. |
| 2016/0072558 A1 | 3/2016 | Hirsch et al. |
| 2016/0073189 A1 | 3/2016 | Lindén et al. |
| 2016/0095553 A1 | 4/2016 | Shieh |
| 2016/0125892 A1 | 5/2016 | Bowen et al. |
| 2016/0360350 A1 | 12/2016 | Watson et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0095202 A1* | 4/2017 | Facteau .................. H04R 25/02 |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0112671 A1 | 4/2017 | Goldstein |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0257698 A1 | 9/2017 | Boesen et al. |
| 2017/0258329 A1 | 9/2017 | Marsh |
| 2017/0311097 A1 | 10/2017 | Nielsen et al. |
| 2018/0214041 A1 | 8/2018 | Hidaka et al. |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 11/1981 |
| GB | 2508226 A | 5/2014 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |

(56) References Cited

FOREIGN PATENT DOCUMENTS

| | | |
|---|---|---|
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |
| WO | 2016038887 A1 | 3/2016 |

OTHER PUBLICATIONS

Announcing the $3,333,333 Stretch Goal (Feb. 24, 2014) pp. 1-14.
Ben Coxworth: "Graphene-based ink could enable low-cost, foldable electronics", "Journal of Physical Chemistry Letters", Northwestern University, (May 22, 2013), pp. 1-7.
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is on Facebook (2014), pp. 1-51.
BRAGI Update—Arrival of Prototype Chassis Parts—More People—Awesomeness (May 13, 2014), pp. 1-8.
BRAGI Update—Chinese New Year, Design Verification, Charging Case, More People, Timeline(Mar. 6, 2015), pp. 1-18.
BRAGI Update—First Sleeves From Prototype Tool—Software Development Kit (Jun. 5, 2014), pp. 1-8.
BRAGI Update—Let's Get Ready to Rumble, A Lot to be Done Over Christmas (Dec. 22, 2014), pp. 1-18.
BRAGI Update—Memories From April—Update on Progress (Sep. 16, 2014), pp. 1-15.
BRAGI Update—Memories from May—Update on Progress—Sweet (Oct. 13, 2014), pp. 1-16.
BRAGI Update—Memories From One Month Before Kickstarter—Update on Progress (Jul. 10, 2014), pp. 1-17.
BRAGI Update—Memories From the First Month of Kickstarter—Update on Progress (Aug. 1, 2014), pp. 1-16.
BRAGI Update—Memories From the Second Month of Kickstarter—Update on Progress (Aug. 22, 2014), pp. 1-15.
BRAGI Update—New People @BRAGI—Prototypes (Jun. 26, 2014), pp. 1-9.
BRAGI Update—Office Tour, Tour to China, Tour to CES (Dec. 11, 2014), pp. 1-14.
BRAGI Update—Status on Wireless, Bits and Pieces, Testing—Oh Yeah, Timeline(Apr. 24, 2015), pp. 1-18.
BRAGI Update—The App Preview, The Charger, The SDK, BRAGI Funding and Chinese New Year (Feb. 11, 2015), pp. 1-19.
BRAGI Update—What We Did Over Christmas, Las Vegas & CES (Jan. 19, 2014), pp. 1-21.
BRAGI Update—Years of Development, Moments of Utter Joy and Finishing What We Started(Jun. 5, 2015), pp. 1-21.
BRAGI Update—Alpha 5 and Back to China, Backer Day, On Track(May 16, 2015), pp. 1-15.
BRAGI Update—Beta2 Production and Factory Line(Aug. 20, 2015), pp. 1-16.
BRAGI Update—Certifications, Production, Ramping Up (Nov. 13, 2015), pp. 1-15.
BRAGI Update—Developer Units Shipping and Status(Oct. 5, 2015), pp. 1-20.
BRAGI Update—Developer Units Started Shipping and Status (Oct. 19, 2015), pp. 1-20.
BRAGI Update—Developer Units, Investment, Story and Status(Nov. 2, 2015), pp. 1-14.
BRAGI Update—Getting Close(Aug. 6, 2015), pp. 1-20.
BRAGI Update—On Track, Design Verification, How it Works and What's Next(Jul. 15, 2015), pp. 1-17.
BRAGI Update—On Track, On Track and Gems Overview (Jun. 24, 15), pp. 1-19.
BRAGI Update—Status on Wireless, Supply, Timeline and Open House@BRAGI(Apr. 1, 2015), pp. 1-17.
BRAGI Update—Unpacking Video, Reviews on Audio Perform and Boy Are We Getting Close(Sep. 10, 2015), pp. 1-15.
Healthcare Risk Management Review, "Nuance updates computer-assisted physician documentation solution" (Oct. 20, 2016), pp. 1-2.
Hoyt et. al., "Lessons Learned from Implementation of Voice Recognition for Documentation in the Military Electronic Health Record System", The American Health Information Management Association (2017), pp. 1-8.
Hyundai Motor America, "Hyundai Motor Company Introduces a Health + Mobility Concept for Wellness in Mobility", Fountain Valley, Californa (2017), pp. 1-3.
International Search Report & Written Opinion, PCT/EP2016/070231 (Nov. 18, 2016) 12 pages.
Last Push Before the Kickstarter Campaign Ends on Monday 4pm CET (Mar. 28, 2014), pp. 1-7.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014), pp. 1-14.
Stretchgoal—The Carrying Case for The Dash (Feb. 12, 2014), pp. 1-9.
Stretchgoal—Windows Phone Support (Feb. 17, 2014), pp. 1-17.
The Dash + The Charging Case & The BRAGI News (Feb. 21, 14), pp. 1-12.
The Dash—A Word From Our Software, Mechanical and Acoustics Team + An Update (Mar. 11, 2014), pp. 1-7.
Update From BRAGI—$3,000,000—Yipee (Mar. 22, 2014), pp. 1-11.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).

* cited by examiner

FIG. 9

DISPOSABLE SENSOR ARRAY WEARABLE DEVICE SLEEVE SYSTEM AND METHOD

PRIORITY STATEMENT

This application is a continuation of U.S. Non-Provisional patent application Ser. No. 15/692,681, filed on Aug. 31, 2017 which claims priority to U.S. Provisional Patent Application 62/382,043, filed on Aug. 31, 2016, all entitled Disposable Sensor Array Wearable Device Sleeve System and Method, hereby incorporated by reference in their entirety.

FIELD OF THE INVENTION

The present invention relates to wearable devices. More particularly, but not exclusively, the present invention relates to earpieces.

BACKGROUND

Sensors installed within electrical devices are prone to premature failure, requiring replacement of the nonfunctioning sensor or even the electrical device itself. Replacement of a defective sensor, however, may be difficult due to the fact that many sensors are either integrated with or contained within the electrical device. What is needed is an easily replaceable sensor or sensor array capable of operatively connecting to an electrical device while retaining its full functionality.

SUMMARY

Therefore, it is a primary object, feature, or advantage of the present invention to improve over the state of the art.

It is a further object, feature, or advantage of the present invention to allow for cost-effective replacement of one or more sensors of a wearable device.

It is a still further object, feature, or advantage of the present invention to allow for replacement of one or more sensors of a wearable device without having to directly remove or replace a sensor installed within the wearable device.

Another object, feature, or advantage is to provide the ability to enhance one or more sensor functions of a wearable device.

Yet another object, feature, or advantage is to provide the ability to enhance one or more sensor functions of a wearable device without the need to replace a sensor directly installed on the wearable device.

In one implementation, a removable wearable device sleeve sized and shaped for fitting to a wearable device includes a sleeve body, one or more sensors integrated into the sleeve body, and an interface integrated into the sleeve body for operative communication between the at least one sensor and the wearable device.

One or more of the following features may be included. The wearable device may be an earpiece and the removable wearable device sleeve may be a removable earpiece sleeve. The removable earpiece sleeve may comprise a sleeve body having a front element having a first aperture, a back element having a second aperture, at least one side element, and a tubular element having a first end connected to the back element and a second end positioned away from the back element having a third aperture, wherein the front element, the back element, each side element, and the tubular element define a cavity to encase an earpiece. The removable earpiece sleeve may have one or more sensors integrated into the removable earpiece sleeve. One or more of the sensors may be a physiological sensor.

In another implementation, a removable sleeve includes a sleeve body having a front element having a first aperture, a back element having a second aperture, at least one side element, and a tubular element having a first end connected to the back element and a second end positioned away from the back element and having a third aperture, wherein the front element, the back element, each side element, and the tubular element define a cavity to encase an earpiece, an interface integrated into the sleeve body, and a sensor integrated into the removable sleeve, wherein the sensor communicates sensor readings to the wearable device through the interface. One or more of the following features may be included. The tubular element may further comprise a portion of the second aperture. The interface may provide for powering the sensor from the wearable device. The removable sleeve may be a removable earpiece sleeve.

In another implementation, a method of placing a sensor configured to communicate with a wearable device onto the wearable device includes providing a removable sleeve comprising the sensor, wherein the removable sleeve further comprises a front element having a first aperture, a back element having a second aperture, at least one side element, and a tubular element having a first end connected to the back element and a second end positioned away from the back element having a third aperture, wherein the front element, the back element, each side element, and the tubular element define a cavity; and inserting the wearable device through the first aperture of the front element into the cavity of the removable sleeve to provide a removable wearable device sleeve. One or more of the following features may be included. The wearable device may be an earpiece. The tubular element may further comprise a portion of the second aperture. The method may further comprise removing an old removable sleeve from the wearable device.

In another implementation, a removable sleeve includes a sleeve body having a front element having a first aperture, a back element having a second aperture, at least one side element, and a tubular element having a first end connected to the back element and a second end positioned away from the back element having a third aperture, wherein the front element, the back element, each side element, and the tubular element define a cavity to encase an earpiece and an interface integrated into the sleeve body. One or more of the following features may be included. The tubular element may further comprise a portion of the second aperture. The removable sleeve may be a removable earpiece sleeve.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an object, feature, or advantage stated herein.

DETAILED DESCRIPTION

Figure 1:
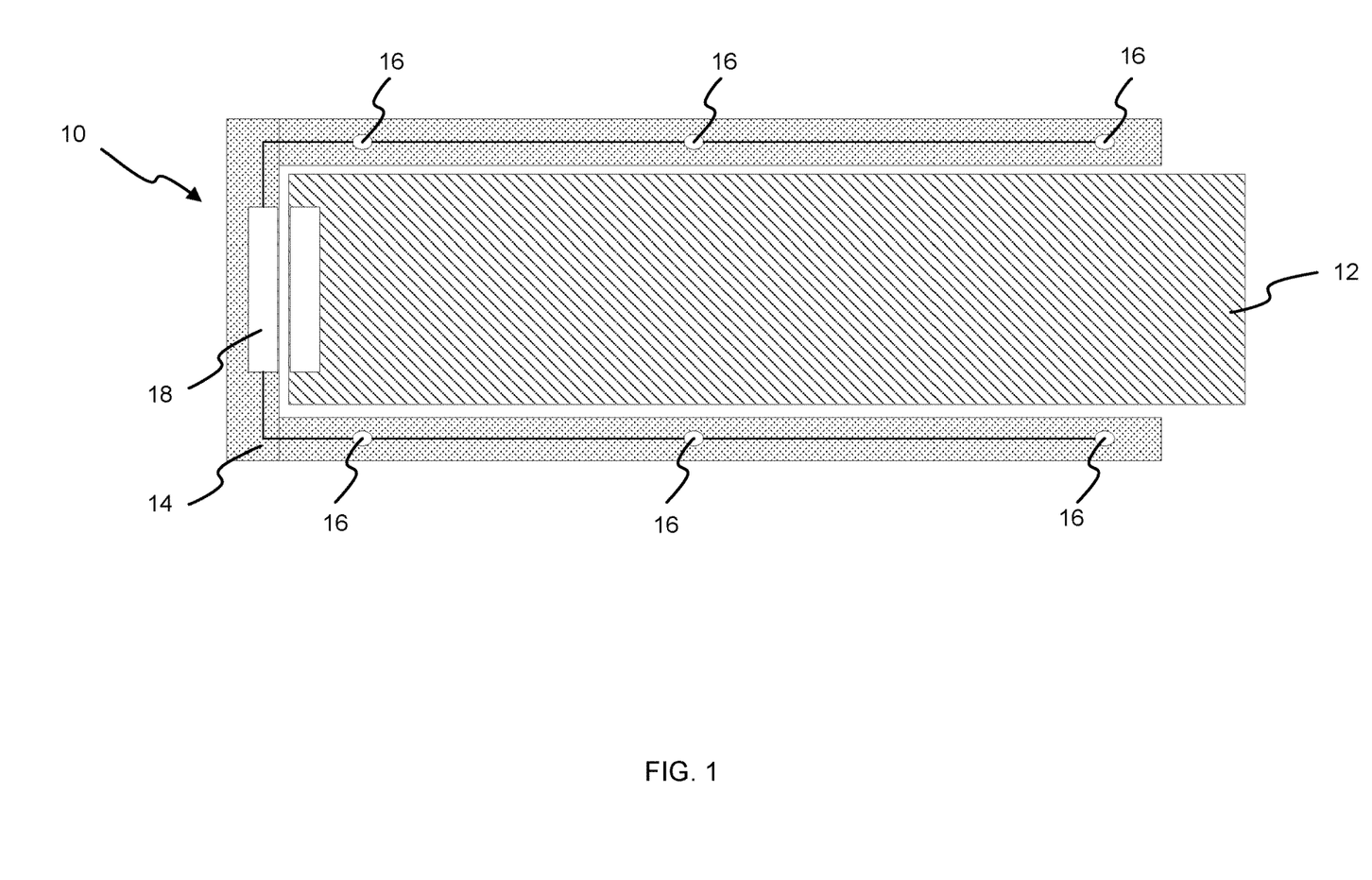
FIG. 1 shows a block diagram of an embodiment of the removable wearable device sleeve.
Figure 2:
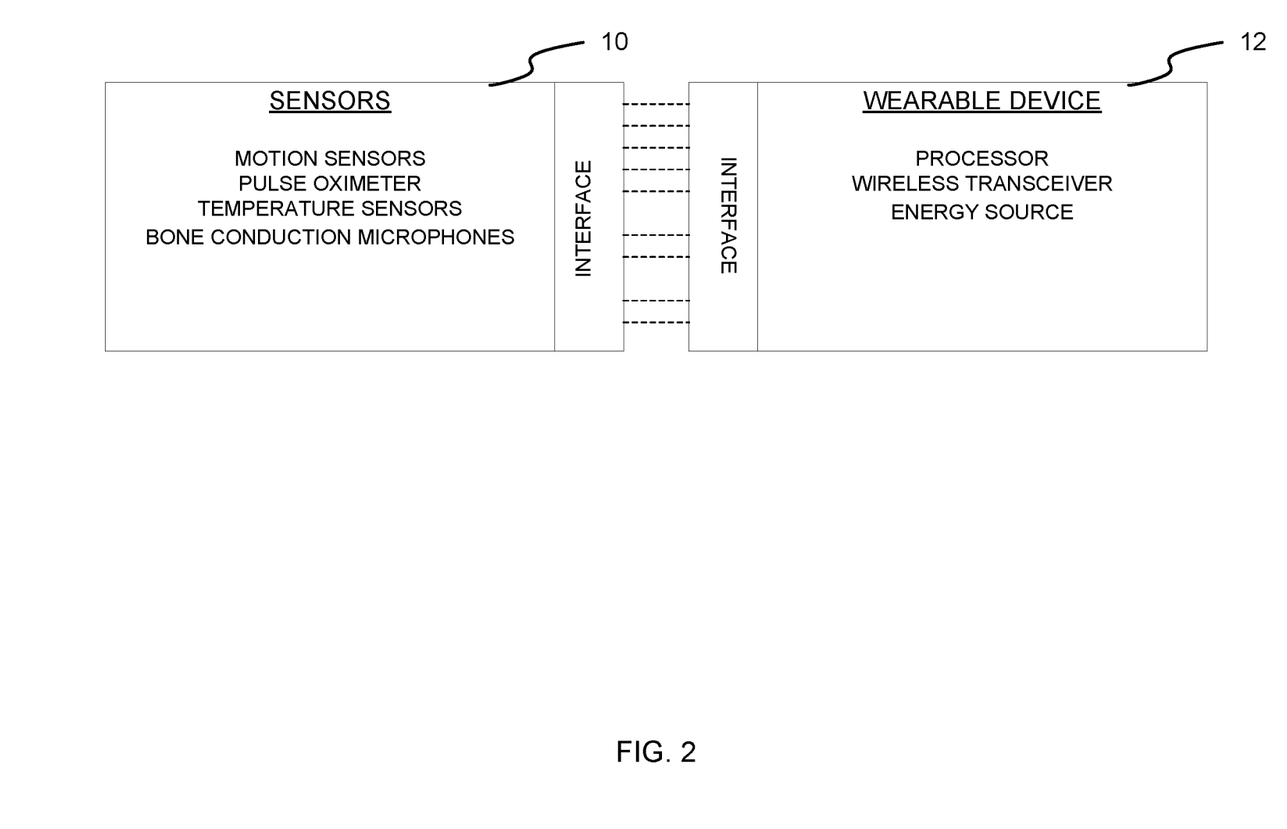
FIG. 2 shows the sleeve interface and the types of interactions that may occur through the interface between a sensor integrated within the sleeve body and a wearable device.

FIG. 1 shows a block diagram of one embodiment of the removable wearable device sleeve 10 and its relationship with a wearable device 12. The removable wearable device sleeve 10 comprises a sleeve body 14, at least one sensor 16 integrated into the sleeve body 14, and an interface 18 integrated into the sleeve body for operative communication between one or more sensors 16 and the wearable device 12. The wearable device 12 may fit substantially within the sleeve body 14 and may interact with the interface 18 of the removable wearable device sleeve 10 to provide energy or facilitate data transfer. The wearable device 12 may comprise one or more earpieces, a headset, headgear, belts, necklaces, bracelets, shirts, shoes, watches, legwear, or wearable rings, as seen in FIG. 2. The sleeve body 14 may be composed of one or more of any type of flexible material, which may include rubber, latex, synthetic plastic, natural fiber-based materials, plexiglass, or any other type of organic or synthetic polymer. More than one type of material may be used in order to take advantage of the different properties of each material. For example, an inner layer of the sleeve body 14 may be composed of latex while an outside layer may be composed of rubber in order to mitigate the chance a user may have an allergic reaction due to the presence of the latex. In addition, the sleeve body 14 may be composed of materials having a high tensile strength to resist tearing due to either repeated attachment and removal of the removable wearable device sleeve 10 or overstretching of the sleeve body 14 itself. The sensors 16 may be integrated into the sleeve body 14 at any position within the sleeve body 14 conducive to making a sensor reading. The sensors 16 integrated within the sleeve body may include a bone microphone, a temperature sensor, a pulse oximeter, a motion sensor, or any combination thereof, and the list is non-exclusive. One or more sensors 16 may also work together to enhance the functionality of a wearable device 12. For example, one of the sensors 16 may be an EMG sensor calibrated to sense electrical activity in the user's facial muscles, while a magnetometer may sense one or more head movements, wherein the sensor readings from both sensors may be communicated to the wearable device 12 to be used to calibrate a facial gesture used to control one or more functions of the wearable device 12. In addition, the sensors 16 may comprise part of a sensor installed on the wearable device 12 or may work in tandem with one or more sensors of the wearable device 12. For example, a removable wearable device sensor 16 may be a temperature sensor and a sensor installed on the wearable device 12 may be a humidity sensor, wherein each sensor work in tandem to provide localized weather information to the user of the wearable device. An interface 18 may be integrated into the sleeve body 14 and may provide for data communication and power. For example, one or more sensors 16 may communicate sensor readings across the interface to the wearable device 12 and the wearable device may provide electrical power to one or more of the sensors 16 integrated within the sleeve body 14.

FIG. 2 illustrates a block diagram of an interface 18 interacting with an interface of a wearable device 12. The interface 18 may communicate data from one or more sensors to the wearable device 12, and the data may be communicated continuously or discretely. The data communicated to the wearable device may comprise sensor readings related to temperature, humidity, user motion, motion related to outside objects, a user's heart rate, internal body sounds, luminescence, or any other number of indicia which may be of interest to the user or a third party. One or more different types of sensors readings may be communicated. For example, one sensor 16 (e.g. a bone conduction microphone) on the sleeve body 14 positioned proximate to a user's ear may sense internal body sounds for audio transparency purposes and communicate the sensor readings continuously, another sensor 16 (e.g. an MEMS gyroscope) may sense head and neck movement, which may be communicated discretely as the user moves his or her head, and another sensor 16 positioned on a portion of the sleeve body 14 to be inserted into a user's ear canal (e.g. a pulse oximeter) may communicate sensor readings related to a user's heartbeat. Data may also be communicated from the wearable device 12 to one or more sensors 16 via the interface 18 as well. For example, the wearable device 12 may communicate one or more position readings to a motion sensor (e.g. a MEMS gyroscope) 16 in order to properly calibrate the sensor 16 to sense user movements. Energy may also be transmitted via the interface 18 in order to power one or more sensors 16. For example, a battery, a capacitor, or an inductor installed within the wearable device 12 may supply power to one or more sensors 16 on either a continuous or as-needed basis depending on the setup of the wearable device 12 and/or the needs of the sensors 16. One or more sensors 16 may also obtain power via a voltage generated by thermal differences between the sleeve body 14, the sensors 16, or the interface 18 and the wearable device 12 or the user's body. It should be noted that the sensors may obtain power from sources other than the wearable device 12, such as through radio waves present in the user's surroundings or via solar apparatuses integrated within the sleeve body 14 which may convert sunlight into electricity that can be used to power one or more sensors 16.

Figure 3:
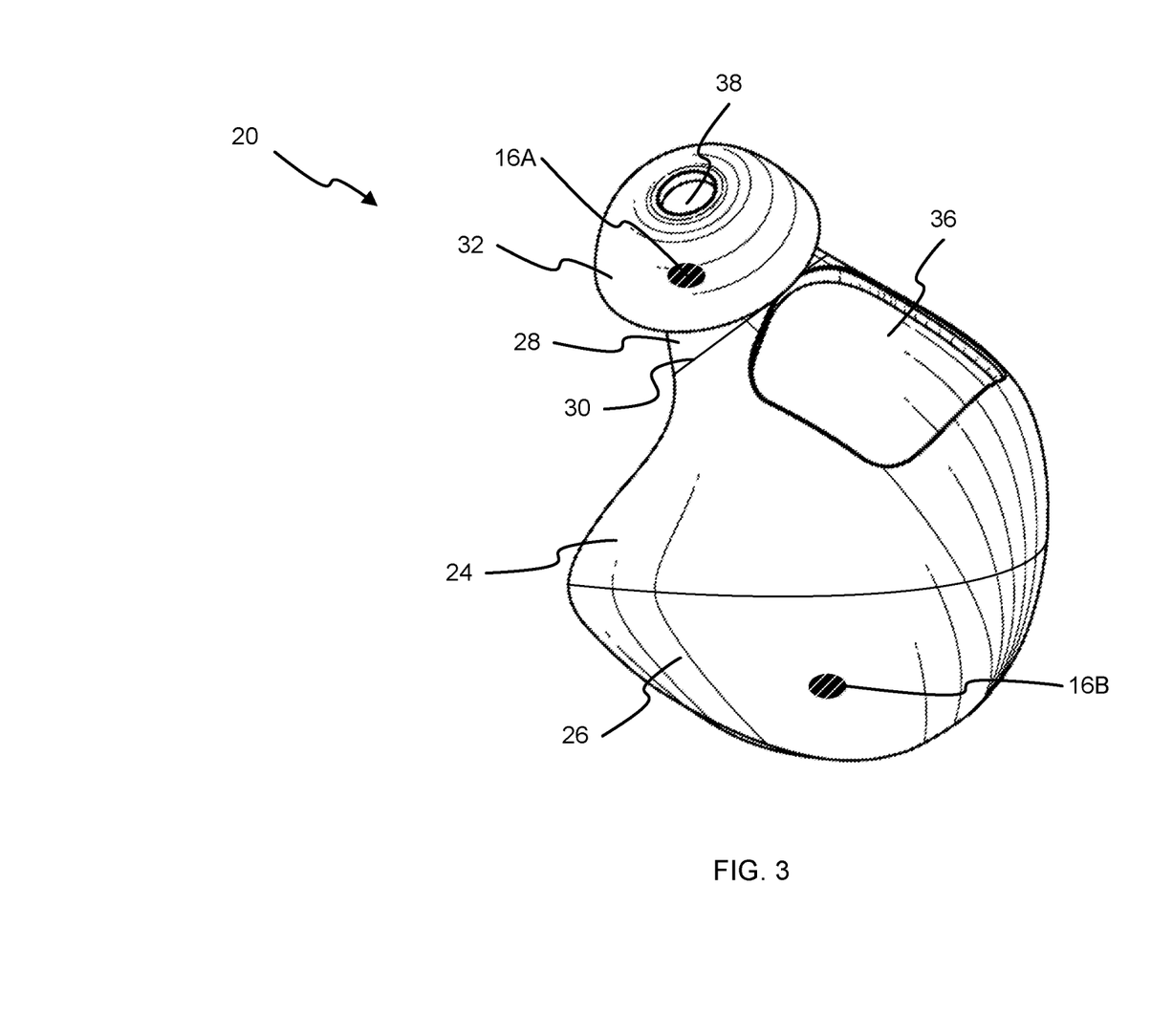
FIG. 3 is an overhead view of a removable earpiece sleeve.
Figure 4:
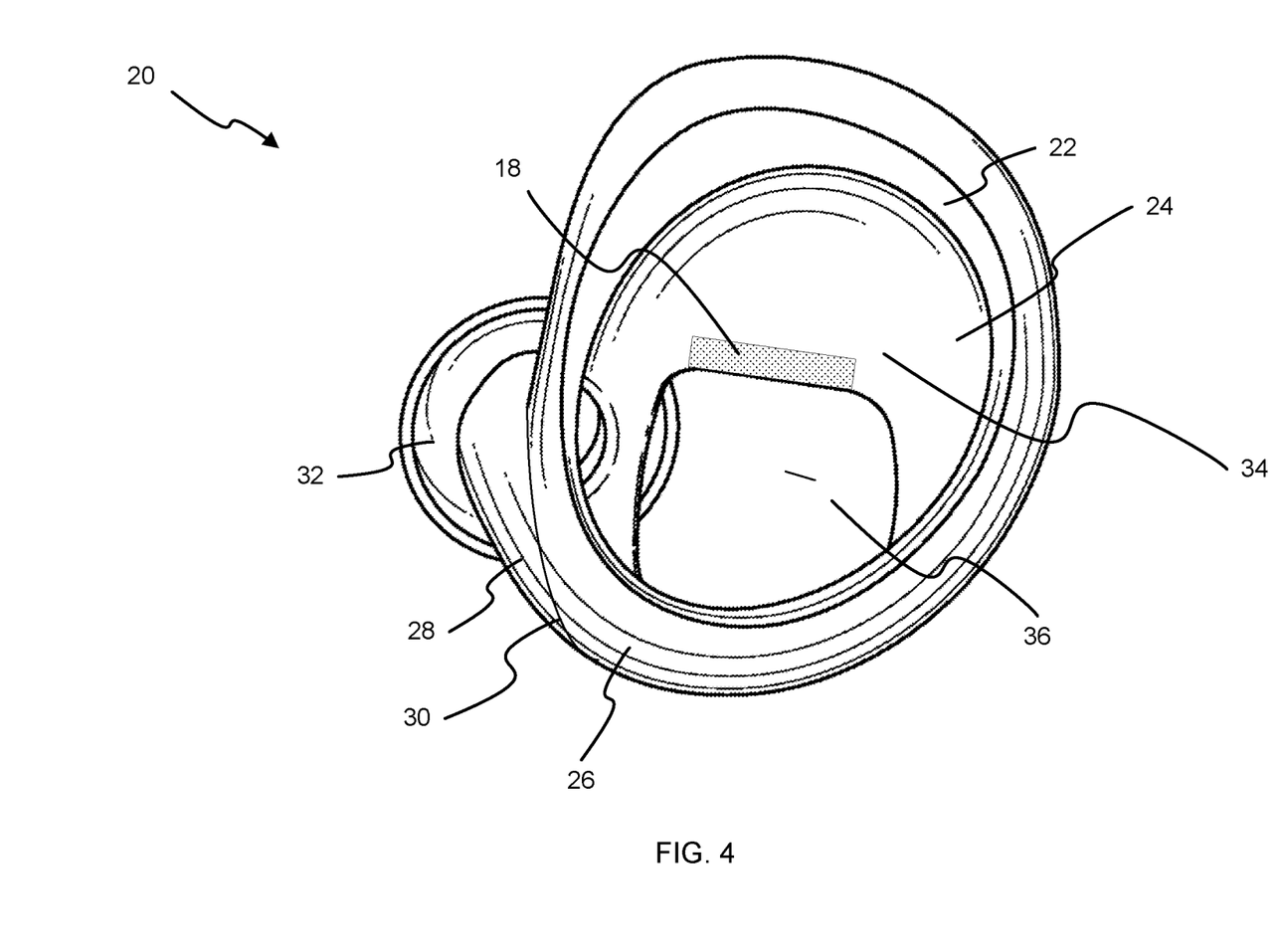
FIG. 4 is a front view of a removable earpiece sleeve.
Figure 5:
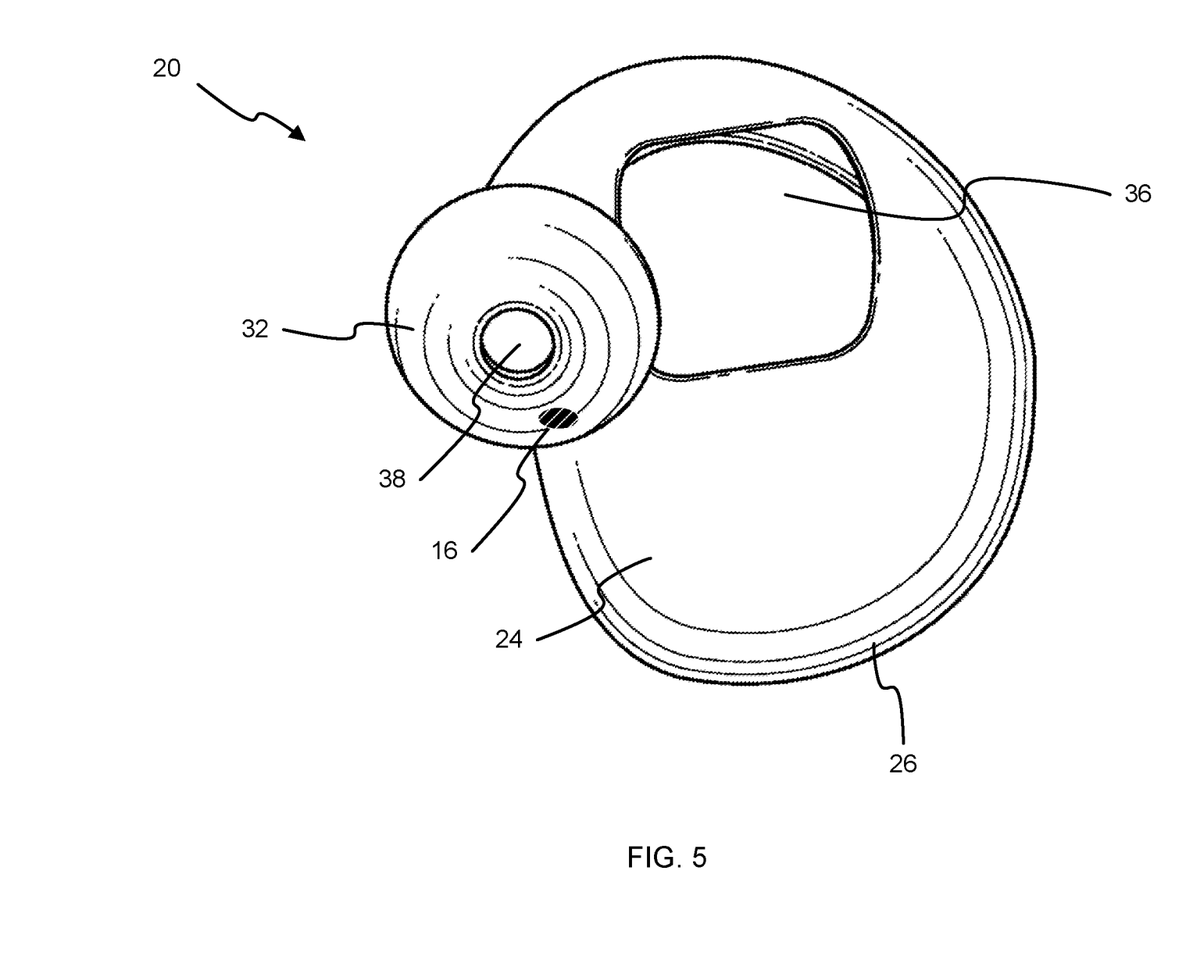
FIG. 5 is a back view of a removable earpiece sleeve.
Figure 6:
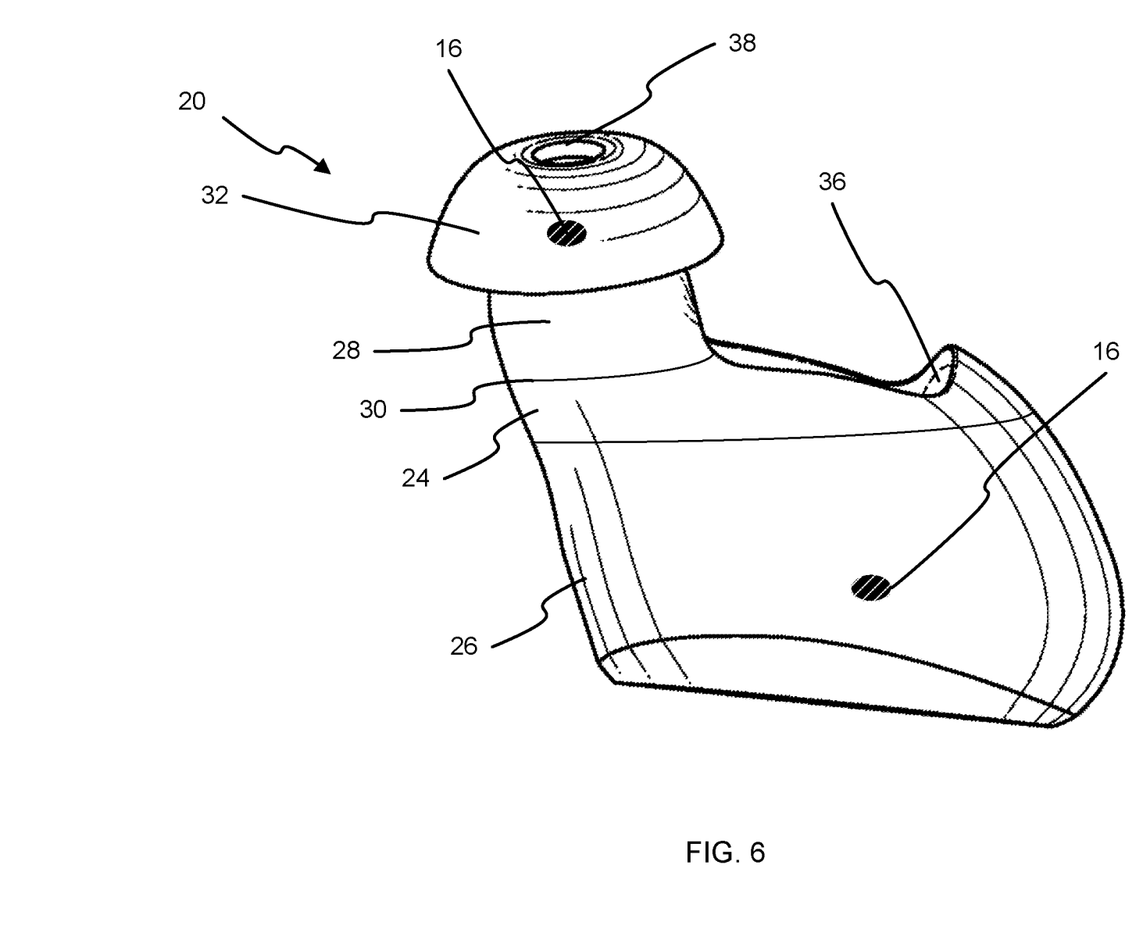
FIG. 6 is a top view of a removable earpiece sleeve.
Figure 7:
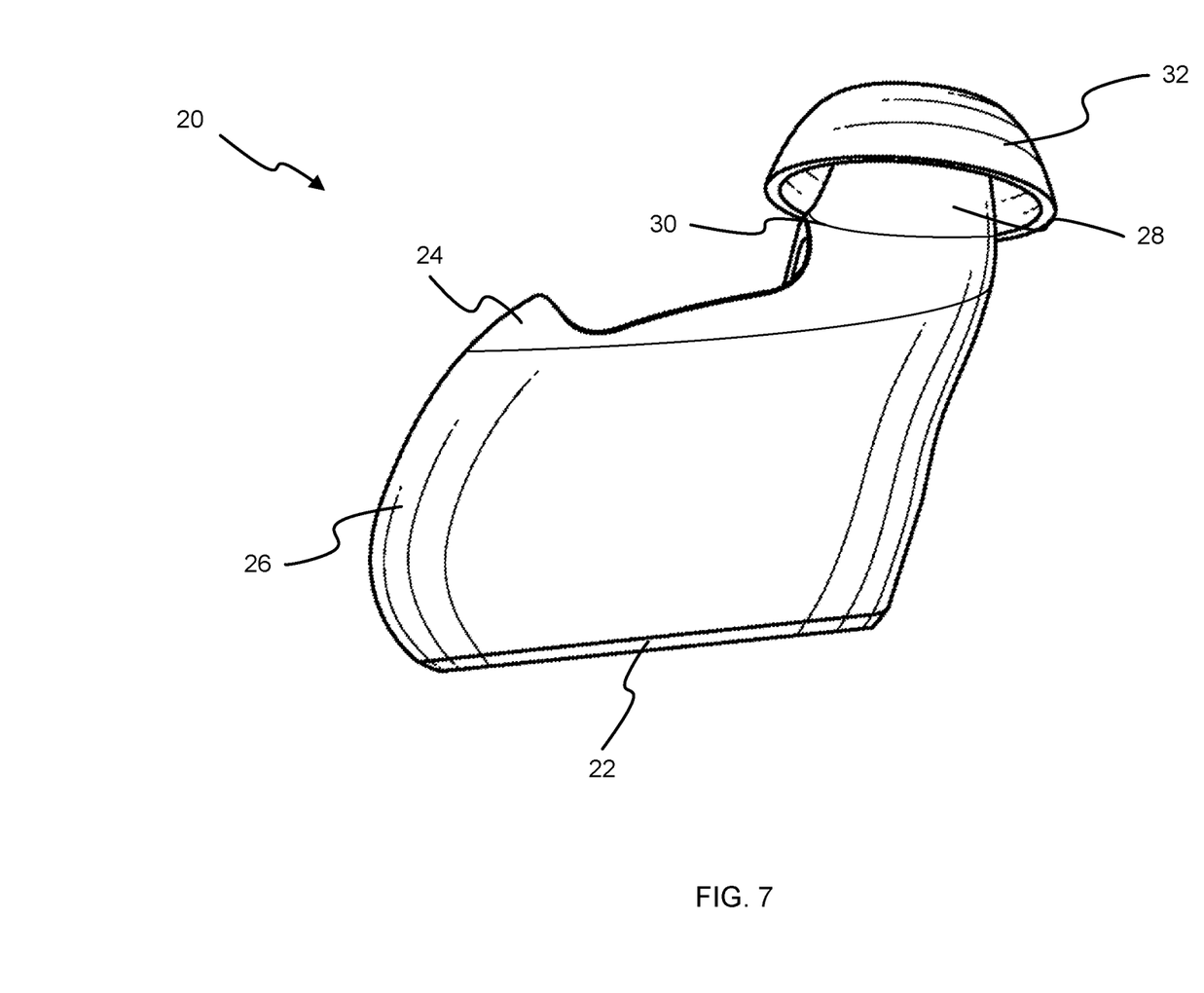
FIG. 7 is a bottom view of a removable earpiece sleeve.
Figure 8:
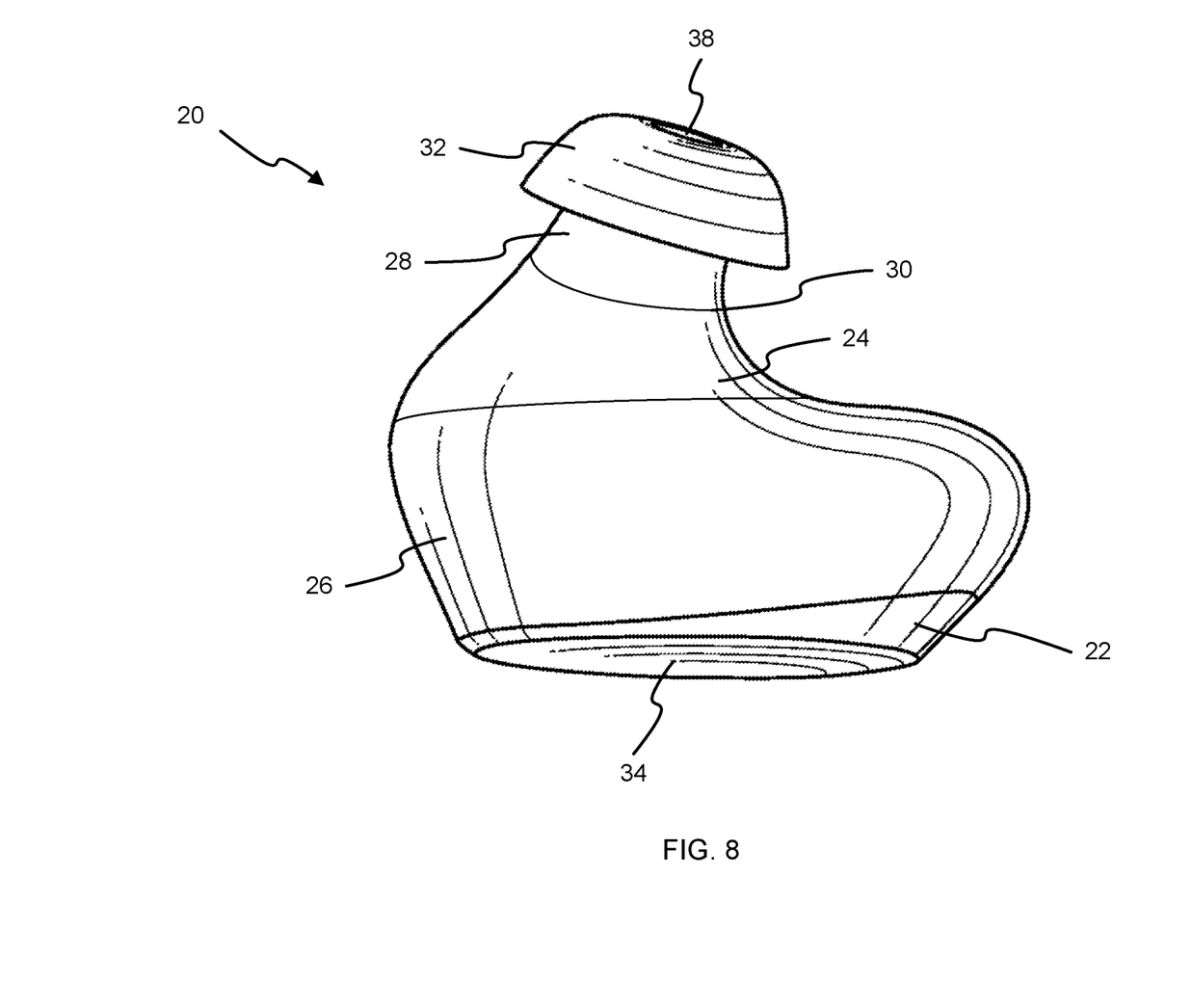
FIG. 8 is a left hand view of a removable earpiece sleeve.
Figure 9:
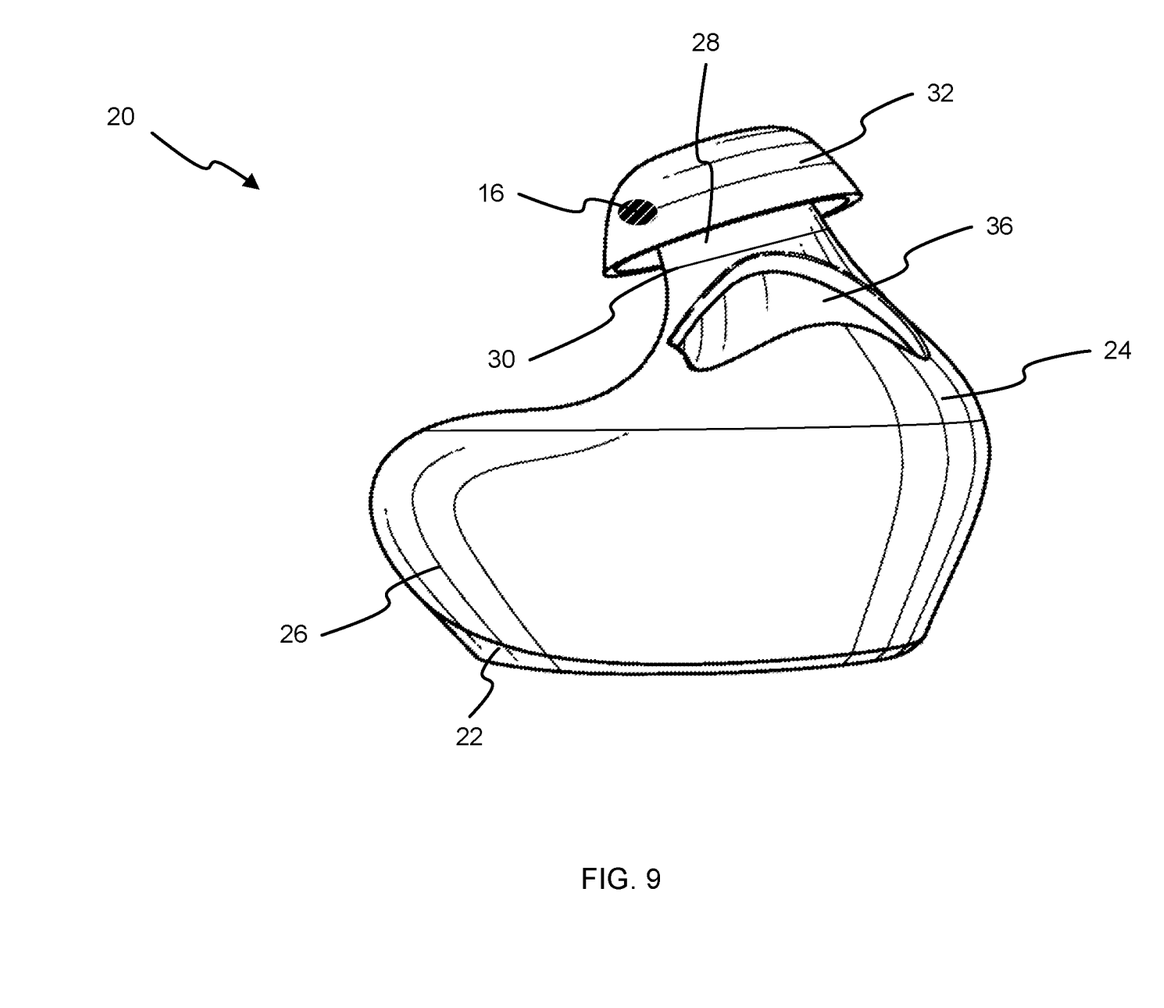
FIG. 9 is a right hand view of a removable earpiece sleeve.

The following figures each show a removable earpiece sleeve 20 from various angles, one embodiment of a removable wearable device sleeve 10. FIG. 3 shows an overhead view of the removable earpiece sleeve 20, FIG. 4 shows a front view of the removable earpiece sleeve 20, FIG. 5 shows a back view of the removable earpiece sleeve 20, FIG. 6 shows a top view of the removable earpiece sleeve 20, FIG. 7 shows a bottom view of the removable earpiece sleeve 20, FIG. 8 shows a left side view of the removable earpiece sleeve 20, and FIG. 9 shows a right side view of the removable earpiece sleeve 20. The removable earpiece sleeve 20 comprises a front element 22 having a first aperture 34, a back element 24 having a second aperture 36, one or more side elements 26, and a tubular element 28 having a first end 30 connected to the back element 24 and a second end 32 positioned away from the back element 24 having a third aperture 38, wherein the front element 22, the back element 24, each side element 26, and the tubular element 28 define a cavity to encase an earpiece. The first aperture 34 is at a distal end of the sleeve, so for example, when the sleeve is placed on an earpiece which is then fitted to a user, the first aperture 34 is at a distal end of the device, facing away from the user. The third aperture 38 would similarly be at the proximal end of the sleeve, inserted into an external auditory canal of the user.

The removable earpiece sleeve 20 may also have one or more sensors 16 positioned throughout the sleeve 20. It may be noted, however, that the removable earpiece sleeve 10 does not need sensors installed within the sleeve. The perimeter of the front element 22 may be any size suitable to allow a user to see the front of an earpiece when an earpiece is encased within the removable earpiece sleeve 20. The first aperture 34 may be any size suitable for an earpiece to fit through and may substantially encompass the front element 22. The back element 24 may be sized to be smaller than or substantially similar to the front element 22, though a back element 24 sized substantially larger than the front element 22 would make it difficult to remove an earpiece from the removable earpiece sleeve 20 via the first aperture 34. The back element may have a second aperture 36 through which an earpiece may interface with a smart case or another electronic device capable of providing data communication, data transfer, and/or power to the earpiece. The second aperture 36 may also provide for user interaction with the earpiece, such as gesture control. In addition, the second aperture 36 may extend into the tubular element 28 as well. One or more side elements 26 connect the front element 22 to the back element 24, and may range from one side element (e.g. a cylindrical shaped sleeve) to theoretically hundreds of elements, and each side element 26 need not connect the front element 22 to the back element 24; the side elements 26 may, for example, be composed of a plurality of hexagons, where only the top layer and bottom layer of hexagons directly touches the front element 22 or the back element 24. The tubular element 28 is connected to the back element 24 via a first end 30 with a second end 32 positioned away from the back element 24 and having a third aperture 38. The tubular element 28 may be sized to fit a component of an earpiece designed to fit within a user's ear canal, and the third aperture 38 may provide an avenue for sound communicated by an earpiece to reach the user's tympanic membrane. The front element 22, the back element 24, each side element 26, and the tubular element 28 may define a cavity for which to encase an earpiece. The cavity may be shaped to fit a specific earpiece or may be shaped to partially or substantially encase earpieces of different sizes or shapes, and the earpiece may be placed into the cavity through the first aperture 34. If the user wishes to replace the removable earpiece sleeve 20 for any reason, for example, if one of the sensors on either the earpiece or the removable earpiece sleeve 20 suffers a loss of functionality or if the sleeve suffers a loss of functionality due to wear and tear, the earpiece may be removed through the first aperture 34, through the second aperture 36, or though ripping or tearing the removable earpiece sleeve 20 off of the earpiece. In addition, a removable earpiece sleeve 20 may be replaced if the user desires to improve or alter the functionality of an earpiece through the use of one or more new sensors on a new removable earpiece sleeve 20 even if the sensors in the original sleeve and the earpiece are still functional.

It should also be understood that various sensors may be positioned on different portions of the sleeve. For example, in FIG. 3 a sensor 16A such as a physiological sensor is positioned near the second end 38 and may be positioned to fit against a wall of an external auditory canal of a user. Another sensor 16B which may also be a physiological sensor may be placed more distally.

A method placing a sensor configured to communicate with a wearable device onto the wearable device is provided.

First, a removable sleeve having at least one or more sensors is provided, wherein the removable sleeve further comprises a front element having a first aperture, a back element having a second aperture, at least one side element, and a tubular element having a first end connected to the back element and a second end positioned away from the back element and having a third aperture, wherein the front element, the back element, each side element, and the tubular element define a cavity. The removable sleeve may be composed of one or more of any type of flexible material that has sufficient tensile strength to resist tearing and is resistant to fatigue, and each sensor may be positioned at any location on the removable sleeve conducive to facilitating a sensor reading. The first aperture may be sized to allow a wearable device to be inserted into the cavity, and the second aperture may permit the wearable device to interface with one or more electronic devices to, for example, recharge or transfer data. The front element, the back element, and each side element may be sized to fit a specific wearable device or to partially or substantially encase a wearable device, and more than one side element may be present. The tubular element may be located at any position on the back element and the third aperture may help facilitate audio communication from a speaker or communication unit of a wearable device if a wearable device is fitted to the removable sleeve. If a sleeve is already present on the wearable device, the old sleeve is removed from the wearable device. The old sleeve may be removed due to the malfunction or failure of one or more sensors on either the old sleeve or the wearable device, the malfunction or failure of one or more functions of the wearable device, or a mechanical failure of the old sleeve itself. If a sleeve was not already present on the wearable device, or if a sleeve was present on the wearable device and removed, then, the wearable device may be inserted into the cavity of the removable sleeve through the first aperture to provide a removable wearable device sleeve. The cavity may be shaped to fit the wearable device or may be shaped to approximate a fit for a random wearable device, and the cavity may encase only a portion of the wearable device. In addition, the removable wearable device sleeve may enhance one or more sensor functions of the wearable device when worn, and may also streamline one or more functions of the wearable device. Therefore, a removable wearable device sleeve and related methods have been shown and described.

What is claimed is:

1. A system comprising:
    a wireless earpiece, the wireless earpiece comprising a wireless earpiece body sized and shaped for fitting into an ear of a user, the wireless earpiece body having a distal end and a proximal end;
    a removable sleeve formed of a flexible material and comprising a sleeve cavity within the removable sleeve, the sleeve cavity is configured to encase the wireless earpiece body such that the removeable sleeve when fit over the wireless earpiece body and when the wireless earpiece is within the ear of the user, the sleeve cavity is encasing the wireless earpiece body and the removable sleeve is in contact with the ear of the user;
    a first interface integrated into the removeable sleeve and configured to communicate with a second interface integrated into the wireless earpiece;
    a plurality of sensors integrated into the removable sleeve such that the plurality of sensors are in contact with the ear of the user, wherein each of the plurality of sensors are electrically connected to the first interface and the plurality of sensors communicates sensor readings to the wireless earpiece through the first interface integrated into the removeable sleeve; and the removable sleeve within a plurality of removable sleeves, each removable sleeve formed of a plurality of sensors integrated into the removable sleeves, wherein at least one removeable sleeve has at least one sensor in its plurality of sensors not in the plurality of sensors on at least one other removable sleeve.

2. The system of claim 1, wherein the first sensor comprises a physiological sensor.

3. The system of claim 2, wherein the physiological sensor is positioned such that when the removable sleeve is fitted to the wireless earpiece and seated within the ear of the user, the physiological sensor is positioned against a wall of an external auditory canal of the user.

4. The system of claim 1, wherein the removable sleeve has an opening at the proximal end and an opening at an opposite distal end, the opening at the distal end larger than the opening at the proximal end.

5. The system of claim 4, wherein the first interface is configured to convey power to the plurality of sensors from the earpiece through the first interface.

6. The system of claim 1, wherein the first sensor comprises a bone microphone.

7. The system of claim 1, wherein the first sensor comprises a temperature sensor.

8. The system of claim 1, wherein the first sensor comprises a pulse oximeter.

9. The system of claim 1, wherein the first sensor comprises a motion sensor.

10. The system of claim 1, wherein the first sensor comprises a gyroscope.

11. The system of claim 1, wherein the removeable sleeve comprising a front element having a first aperture, a back element having a second aperture, at least one side element, and a tubular element having a first end connected to the back element and a second end positioned away from the back element having a third aperture.

12. A system comprising:

a wireless earpiece, the wireless earpiece comprising a wireless earpiece body sized and shaped for fitting into an ear of a user, the wireless earpiece body having a distal end and a proximal end;

a removable sleeve comprising a sleeve body having a front element having a first aperture, a back element having a second aperture, at least one side element, and a tubular element having a first end connected to the back element and a second end positioned away from the back element having a third aperture, wherein the front element, the back element, each side element, and the tubular element define a cavity to conformingly fit over the wireless earpiece such that a distal end of the sleeve body is positioned at the distal end of the wireless earpiece body and a proximal end of the sleeve body is positioned at the proximal end of the wireless earpiece body, the removable sleeve formed of a flexible material such that the removeable sleeve when fit over the wireless earpiece body and when the wireless earpiece is within the ear of the user, the removeable sleeve is in contact with the ear of the user;

a first interface integrated into the removeable sleeve and configured to communicate with a second interface integrated into the wireless earpiece; and a plurality of sensors integrated into the removable sleeve such that the plurality of sensors are in contact with the ear of the user, wherein each of the plurality of sensors are electrically connected to the first interface and the plurality of sensors communicates sensor readings to the wireless earpiece through the first interface integrated into the removeable sleeve.

13. The system of claim 12, wherein when the removal sleeve is fit over the wireless earpiece body and when the wireless earpiece is within the ear of the user, the removeable sleeve is in contact with the ear of the user and at the second aperture of the removable sleeve, the wireless earpiece body is in contact with the ear of the user.

14. The system of claim 12, wherein the first sensor comprises a physiological sensor positioned such that when the removable sleeve is fitted to the wireless earpiece and seated within the ear of the user, the physiological sensor is positioned against a wall of an external auditory canal of the user.

15. The system of claim 12, wherein the first interface is configured to convey power to the plurality of sensors from the earpiece through the first interface.

16. The system of claim 12, wherein the first sensor comprises a bone microphone.

17. The system of claim 12, wherein the first sensor comprises a temperature sensor.

18. The system of claim 12, wherein the first sensor comprises a pulse oximeter.

19. The system of claim 12, wherein the first sensor comprises a motion sensor.

20. The system of claim 12, wherein the first sensor comprises a gyroscope.

21. The system of claim 12, comprising at least two removable sleeves, each removable sleeve formed of a plurality of sensors integrated into the removable sleeves, wherein at least one removeable sleeve has at least one sensor in its plurality of sensors not in the plurality of sensors on at least one other removable sleeve.

* * * * *